United States Patent [19]

Clingman, Jr. et al.

[11] 4,396,299
[45] Aug. 2, 1983

[54] METHOD AND APPARATUS FOR DETERMINING TOTAL ENERGY FLOW IN A GAS LINE

[75] Inventors: William H. Clingman, Jr.; Lyn R. Kennedy, both of Dallas, Tex.

[73] Assignee: Precision Machine Products, Inc., Dallas, Tex.

[21] Appl. No.: 272,204

[22] Filed: Jun. 10, 1981

[51] Int. Cl.³ .............................................. G01F 1/68
[52] U.S. Cl. ...................................................... 374/37
[58] Field of Search .................................... 374/36, 37

[56] References Cited

U.S. PATENT DOCUMENTS

| | | | |
|---|---|---|---|
| 2,139,768 | 12/1938 | Naiman | 374/36 |
| 2,574,665 | 11/1951 | Schuller | 374/37 |
| 3,777,562 | 12/1973 | Clingman, Jr. | 374/37 |
| 4,359,284 | 11/1982 | Kude et al. | 374/37 |

FOREIGN PATENT DOCUMENTS 8151 2/1980 European Pat. Off. ............... 374/37

*Primary Examiner*—Herbert Goldstein
*Attorney, Agent, or Firm*—Joseph H. Schley; Thomas L. Cantrell; Stanley R. Moore

[57] ABSTRACT

Disclosed are methods and apparatus for measuring and determining the total energy flow, that is, BTUs per minute, of combustible gas flowing through a line such as a pipeline. One method includes taking a continuous sample of the gas slowing through the line which sample is a constant proportion of the gas flowing through the line, and burning the sample in equipment which supplies air to the sample in an amount which maximizes its burning temperature. The flow rate of air which produces the maximum burning temperature of the sample is a flow rate which is directly proportional to the rate of energy flow in the main pipeline. Alternately, the flow rate of air which produces a stoichiometric mixture is directly proportional to the rate of energy flow in the main pipeline. Still further, if an excess of air is flowed to the flame, the amount of excess unconsumed oxygen is also a function of the rate of energy flow in the main pipeline. One or another of these parameters is measured. Also disclosed is equipment capable of effectively performing the several steps of the method.

12 Claims, 6 Drawing Figures

METHOD AND APPARATUS FOR DETERMINING TOTAL ENERGY FLOW IN A GAS LINE

BACKGROUND OF THE INVENTION

The recent large increase in the dollar value of BTUs contained in natural gas, and other combustible gases, has increased the need to measure accurately the total energy flow rate of gas moving through pipe line systems, both at points near the point of use of the gas, and at points which may be remote from the point of use. The conventional methods for determining total energy flow rate at a point in a gas pipeline generally involve the simultaneous (or at least contemporaneous) measurement of several gas parameters which are then employed as inputs into calculations ultimately producing a figure for energy flow. For example, one approach is to measure the pressure drop across an orifice plate in the line to obtain a starting point for calculation of flow rate, and to simultaneously measure the temperature of the flowing gas and its composition at the time (the latter being measured by a gas chromatograph). The composition, pressure and temperature measurements provide the data necessary for calculation of the density of the gas at the orifice plate. The calculated density and the before mentioned pressure drop across the orifice plate provide the data necessary for calculation of the volumetric flow rate. The gas composition measurement, taken together with the known heat of combustion values for various compounds and elements enables one to calculate the heat of combustion per unit volume. Finally, the calculated heat of combustion per unit volume can be multiplied by the calculated volumetric flow rate to give a figure for energy flow rate.

It can be seen that this approach and other similar conventional approaches which involve the making of multiple measurements of gas properties or parameters suffer from the apparent disadvantage that each measurement or type of measurement involves measurement errors. The errors of the multiple measurements accumulate and contribute an error in the final calculated figure, which error may be quite sizable. In addition, each measurement made on the gas involves a measuring entity comprising some quantity of equipment which must be maintained, and further involves periodic calibrating of that equipment to the desired or best possible accuracy. Furthermore, such approaches, to the extent that they involve hand calculations, also present opportunities for calculation errors.

SUMMARY OF THE INVENTION

In accordance with the present invention, methods and apparatus are provided for measuring total energy flow rate of combustible gas flowing in a line. The methods and apparatus for practicing the methods involve making only a single measurement which is of a parameter that stands in constant proportion to the total energy flow rate of the moving gas. The invention involves two basic method steps, and two primary equipment sections for performing those steps.

The first step, and the first equipment section, involves the taking of a continuous or flowing sample of the gas flowing in the pipeline, which sample is a constant fraction of the gas flowing through the line. The equipment section is specially devised to provide this sort of division of gas flow between the main line and the sample line.

The second method step, and the second equipment section, preferably involves burning of the sample with an amount of air which results in the combustion temperature being maximized. When the burning occurs under conditions which maximize the combustion temperature, then the air flow rate producing that condition is proportional to the energy flow in the gas flowing through the main pipe line. In a sense, the sample of combustible gas is "titrated" with air. The present invention thus in part makes use of techniques disclosed and claimed in Clingman U.S. Pat. Nos. 3,777,562 issued Dec. 11, 1973; 4,062,236 issued Dec. 13, 1977; 4,125,018, issued Nov. 14, 1978; and 4,125,123 also issued Nov. 14, 1978. Furthermore, the present invention preferably makes use of a flow measurement system for determining air flow of the kind disclosed and claimed in Kennedy U.S. patent application Ser. No. 100,918, filed Dec. 6, 1979, entitled Method And Apparatus For Measuring And Controlling Volumetric Flow Rate Of Gases In A Line, now U.S. Pat. No. 4,285,245 issued Aug. 25, 1981.

As is brought out below, the second method step may alternately comprise forming a stoichiometric mixture of air and the sample of combustible gas and burning it. The rate of air flow sufficient to produce the stoichiometric mixture is also directly proportional to the energy flow rate in the main pipeline. As a variant on this latter method step, a deliberate excess of air may be flowed to the sample flame, and the residual oxygen flow in the exhaust gas is measured. The level of residual oxygen flow is also a function of the energy flow rate in the main pipeline.

Since the present invention involves the making of only a single measurement, it represents a material advance in the accuracy of determination of total energy flow rate of gas moving through a line, because the stacking up or accumulation measurement errors inherent in methods involving the measurement of multiple parameters is eliminated.

Furthermore, the equipment may be calibrated so that no calculations are necessary to yield a total energy flow rate figure.

The taking of the proportionally constant sample step of the invention may be performed in any satisfactory manner. In some situations, a simple branching of the main gas flow pipeline into a main line and a sample line may be adequate as a matter of hardware to provide for the proportionally constant sampling. In most situations however, such a simple arrangement of hardware will not suffice to provide the uniformity of the proportional sampling desired.

Accordingly, it is preferred that the equipment for the continual taking of a proportionate sample of the gas flowing through the line includes an orifice plate flow meter in the main gas pipeline, a sample line tapped into the main pipeline upstream from the orifice plate, an orifice plate in the sample line, and equipment for adjusting the pressure downstream of both orifice plates to the same value. The downstream pressure equalizing equipment may take any one of several forms as will be made clear in the discussion of the detailed embodiments which follow.

As the discussion below in connection with the detailed preferred embodiments will bring out, a consideration of the orifice equations will reveal that when the pressure drop across each orifice plate is adjusted and maintained at a uniform level, and when the gas temperature and composition at each orifice plate is uniform, and when the up-stream pressures are uniform, all of which conditions being met in accordance with the invention, then the ratio of flow rates between the main gas flow pipeline and the sample line are in a fixed ratio, dependent primarily on relative orifice area.

While it is possible to measure the pressure drops across the main line and sample line orifice plates and to calculate from the pressure drop measurements the respective flow rates, this is not strictly necessary for the routine practice of the invention. What is of interest is not so much the value of the flow rates as the circumstance that the sample line gas flow rate is a constant proportion of the main line gas flow rate, all assuming, of course, that the calibration work involved in initially setting up the equipment has been completed.

As was mentioned above, in accordance with the invention the sample flowing through the sample line is combusted or burned with air. In a preferred embodiment the flow rate of the air for combustion is measured. The air flow rate is varied or adjusted so that the combustion temperatures is at a maximum. When this condition is met, then the air flow rate is directly proportional to the flow rate of energy in the main pipe line. While the maximum temperature method is presently preferred, the alternate methods involving stoichiometric mixtures or deliberate excesses of combustion air may also be employed.

As a matter of equipment, the several apparatuses shown in above mentioned U.S. Pat. Nos. 3,125,123; 4,125,018 and 3,777,562 may be used in various embodiments if suitably modified. In this connection, it should be noted that in said patents a number of the embodiments perform a flow rate measurement step on the gas stream rather than on the air stream, although in each case this procedure is a matter of choice. When such equipment is used in the practice of the present invention, the flow rate measurement of the air stream is the measurement which is of interest and which is, as practical matter, the stream which must be measured. Thus persons with ordinary skill in the art will understand how to modify or alter the equipment shown in the above listed patents to accomodate it to the practice of the present invention.

It should also be noted that the air flow rate which produces a maximum adiabatic flame temperatue is also, within very close limits, equal to the air flow rate which produces a stoichiometric mixture with the particular gas composition flowing through the main pipe line.

This circumstance leads to the alternate manners of performing the second step of the method of the invention which alternates manners have been referred to above. Thus, starting with an excess, the air flow rate may be slowly lowered and monitored by way of an oxygen detector in the exhaust gas from the flame where the sample is burned. When the oxygen detector indicates a sharp decrease in oxygen in the exhaust gas, it is then known that the air flow rate is sufficient to produce a stoichiometric mixture. As another variant manner in performing the second method step, a deliberate excess of air may be flowed to combust with the sample of combustible gas. The oxygen flow in the exhaust gas from that flame can be monitored, and the level of excess flow or remnant in the exhaust gas stream is a linear function, of the energy flow rate in the sample stream, and in the gas stream in the main pipeline.

From the foregoing it can be seen that the primary object of the invention is the provision of methods and apparatus for accurately and conveniently measuring the total energy flow rate of a gaseous fuel moving through a line.

Another object of the invention is to provide methods and apparatus for taking a continual sample of gas from a gas flowing through a main line, which sample is a constant proportion of the gas flowing through the main line.

Still another object of the present invention is to provide a method and apparatus for dividing a flowing gas stream into constantly proportionate streams.

Still another object of the present invention is the provision of methods and apparatus whereby the energy flow rate in a gas flowing through a line may be determined by making only a single measurement.

The manner in which the foregoing and other objects are attained together with other objects and purposes of the invention may best be understood by considering the detailed description which follows, together with the accompanying drawings.

DESCRIPTION OF THE PREFERRED EMBODIMENT

Figure 1:
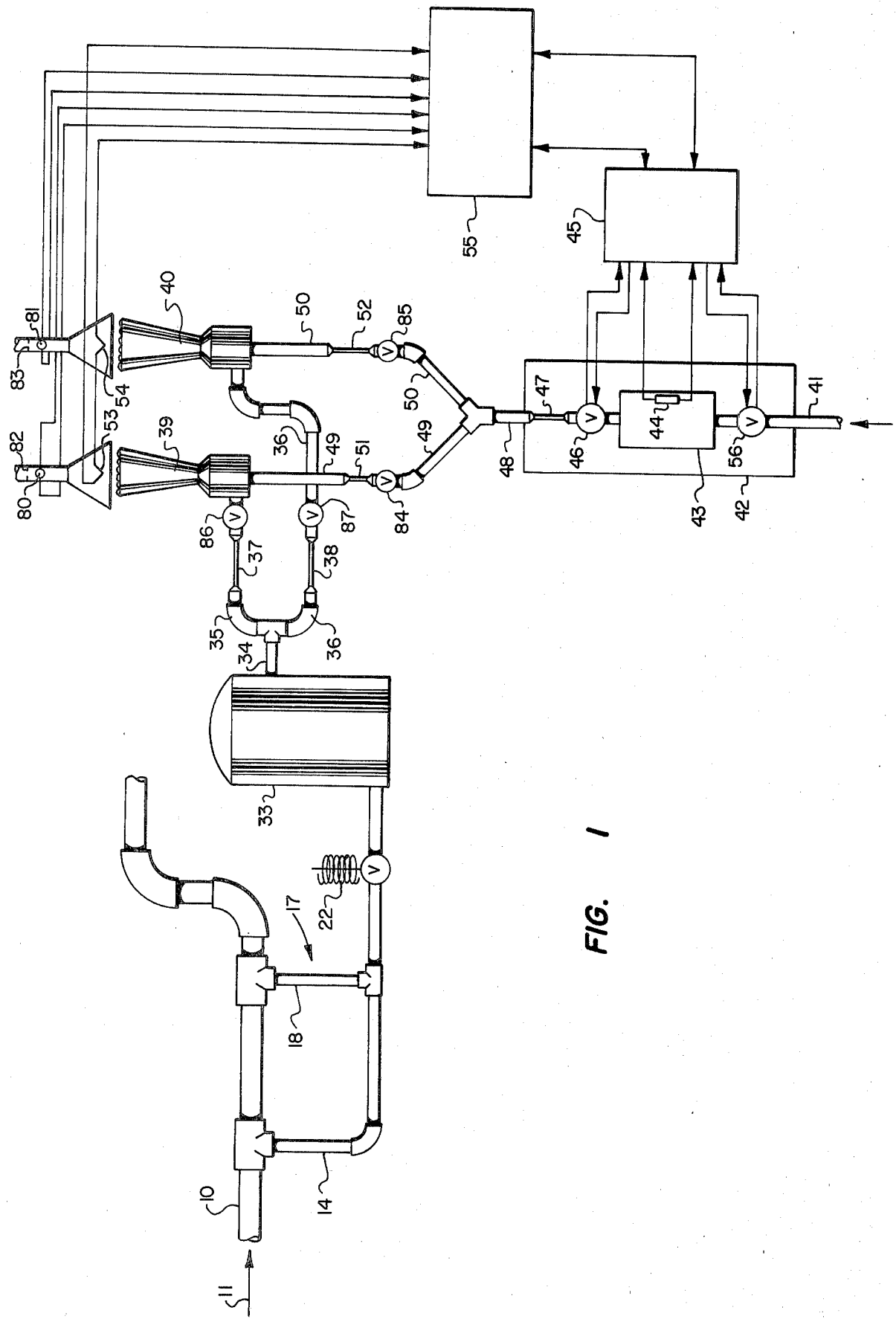
FIG. 1 is a diagramatic elevational view of a system constructed in accordance with the invention and operating to practice the method aspects of the invention.
Figure 2:
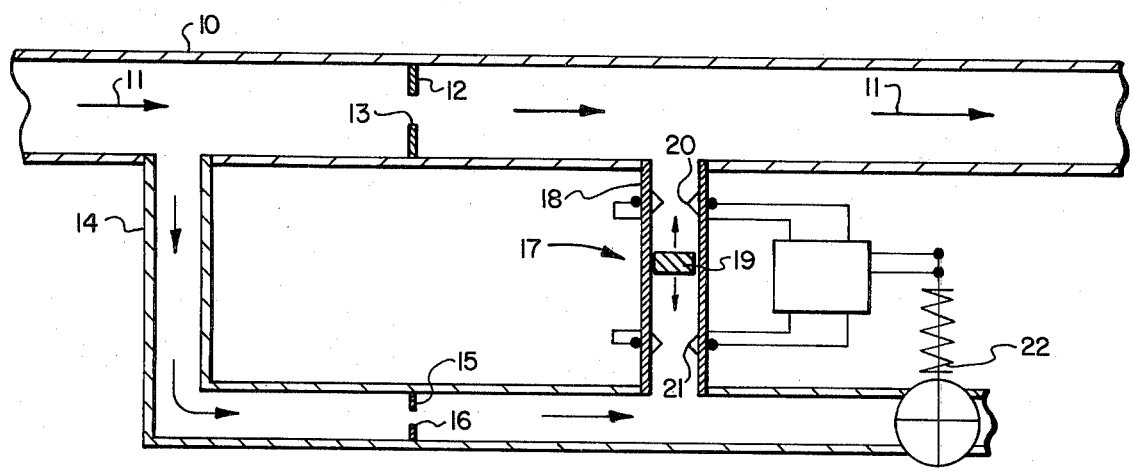
FIG. 2 is a diagramatic elevational view of a portion of the equipment of the embodiment of FIG. 1 namely the proportionate sample gathering equipment.

Attention is first directed to FIGS. 1 and 2 which illustrate the method and equipment of the invention in one preferred form. In these figures a main gas pipeline is designated 10 and the flow of gas through that pipeline from left to right is indicated by arrows 11. In the pipeline is mounted an orifice plate 12 having an orifice opening 13 therein. Upstream of the orifice plate a branch line 14 is tapped into main line 10. The branch line 14 also has an orifice plate 15 mounted therein, and the orifice plate 15 has an orifice opening 16. The equipment described to this point thus consists of a main line with an orifice plate in it and a branch line also having an orifice plate in it.

The equations for gas flow through orifices 12 and 15 are as follows:

$$Q_{12} = K_{12} A_{12} (2gh_{12})^{\frac{1}{2}} \quad (1)$$

$$Q_{15} = K_{15} A_{15} (2gh_{15})^{\frac{1}{2}} \quad (2)$$

Q = rate of flow in cubic feet per second
K = coefficient of discharge
A = orifice area
g = acceleration due to gravity h = differential head across orifice Because of the metalstructure the temperature at both orifice plates will be the same. The gas composition is the same in both cases. The pressures on both sides of orifice 1 are also the same as the corresponding pressures across orifice 6. Thus the gas properties on both sides of the orifice plate are identical in the two cases. The ratio of the two flows is then given by $Q_{15}/Q_{12}$ $$Q_{15}/Q_{12} = (A_{15}/A_{12})(K_{15}/K_{12}) \qquad (3)$$

Reference 1 gives equations for the discharge coefficient $$K_{12} = K_{12}'(1 + E_{12}/R_{d12}) \; ; \; K_{15} = K_{15}'(1 + E_{15}/R_{d15})$$

$R_{di}$ = Reynolds number = $v_i d_i \rho/\mu$
$d_i$ = orifice diameter
$v_i$ = jet velocity in the plane at the orifice
$\rho$ = gas density
$\mu$ = viscosity $$E_i = d_i(830 - 5000b_i + 9000b_i^2 - 4200b_i^3 + B_i) \qquad (4)$$

$D_i$ = pipe diameter
$b_i = d_i/d_i$
where
$B_i = 530/D_i$ for flange taps
$B_i = 875/D_i + 75$ for pipe taps
$A_i K_i$ is the effective area of the jet in the plane of the orifice. Thus, $$v_i = Q_i/A_i K_i$$

It thus follows from (3) that $$v_{12} = v_{15} \text{ and } R_{d12}/d_{12} = R_{d15}/d_{15}$$

Now define the function, F(6) as follows:

$$F(6) = E/d - B$$

The following table was calculated using equation (4)

| b | F(b) |
|---|---|
| .7 | 299 |
| .6 | 163 |
| .5 | 55 |
| .4 | 1 |
| .3 | 27 |
| .2 | 156 |
| .1 | 416 |

The design equations for orifice 6 are now as follows:

FLANGE TAPS:
$$F(b_{15}) + 530/D_{15} = F(b_{12}) + 530/D_{12} \qquad (5)$$

PIPE TAPS: $F(b_{15}) = 875/D_{15} = F(b_{12}) + 875/D_{12}$ $B_{15}$ and $D_{15}$ are chosen so as to minimize the flow through conduit 5 and to satisfy these equations.

Downstream from the orifice plates 12 and 15 respectively main line 10 and branch line 14 are connected by pressure equalizing means designated generally as 17. In the embodiment of FIGS. 1 and 2 this means includes a line 18 interconnected between the main pipe line 10 and branch lines or sample line 14. A piston 19 is positioned to move within connecting line 18. Microswitch points 20 and 21 are positioned in line 18 to be connected by piston 19 when it is in the connecting line 18 in the immediate vicinity of contact points 20 or 21. Downstream in line 14 from the point of interception of line 18 with line 14 there is mounted motorized valve 22.

The operation of the equipment described to this point is as follows:

Assuming that motorized valve 22 is closed, the situation will be that the upstream pressure on orifice plates 12 and 15 will be equal, but the downstream pressure will be unequal. It will be lower in the main line 10 than in branch line 14. In branch line 14 the pressure on the downstream side of orifice plate 15 will be substantially equal to the upstream pressure by reason of the closed condition of valve 22. Under these circumstances piston 19 will move toward contacts 20 and will make the circuit through them. This event actuates motorized valve 22 to open it and it will eventually open sufficiently far that the pressure on the downstream side of orifice plate 15 will be lower than that on the downstream side of orifice plate 12 in main line 10. These conditions will cause piston 19 to move toward contacts 21, and upon closing the circuits through those contacts, will actuate motorized valve 22 to close. Upon its closure the first described set of conditions in the operations will exist once again. The piston thus migrates back and forth between contacts 20 and 21 alternately opening and closing motorized valve 22. Thus, on the average, the pressure downstream of orifice plate 12 and orifice plate 15 is equal, even though at any particular moment the downstream pressures may in fact be unequal.

Figure 3:
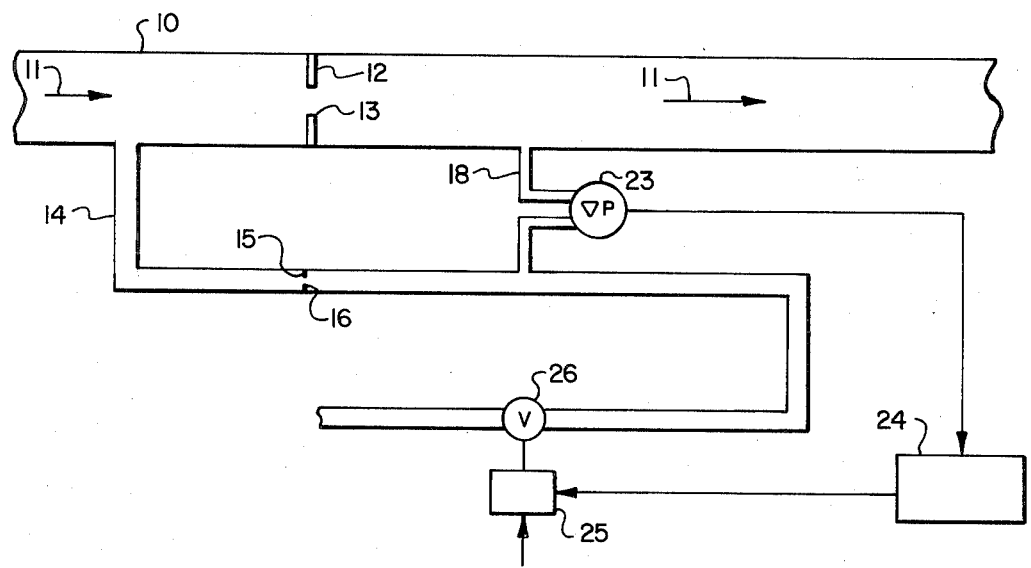
FIG. 3 is a diagramatic elevational view of an alternate form of the equipment for gathering proportionate samples in accordance with the invention.

Attention is now directed to FIG. 3 which shows another set of equipment for accomplishing a division of the gas stream into that flowing in the main pipe line and the proportionate fraction flowing in the sample line 14. In FIG. 3 the same reference characters are used for substantially identical parts.

In the embodiment of FIG. 3 a differential pressure gauge or meter 23 is interposed in line 18 to compare the downstream pressure in main pipe line 10 and sample line 14. A comparison signal is sent to a microprocesser controller 24 where it is conventionally processed to send a signal to motor 25 of motor driven valve 26 to open or close valve 26 in a manner to bring the two downstream pressures to equality.

Figure 4:
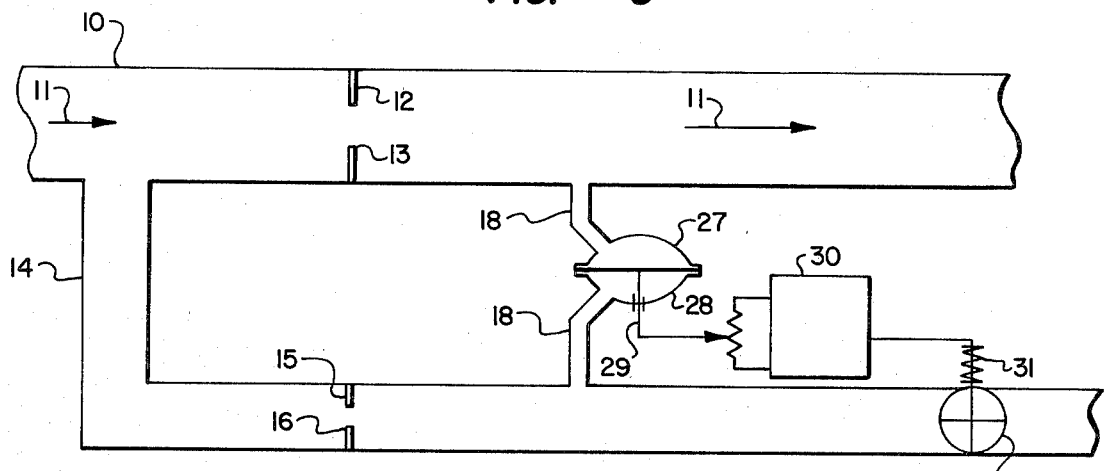
FIG. 4 is a diagramatic elevational view of another alternate form of the equipment for gathering proportionate samples in accordance with the invention.

In FIG. 4 there is illustrated still another set of equipment for performing the proportionate sample taking function. In the embodiment of FIG. 4 there is interposed in line 18 a housing 27 having a diaphragm 28 connected across the interior thereof. A follower 29 is connected to the diaphragm and passes through an opening in the wall of housing 27. The follower carries a wiper working on the slide wire of a potentiometer associated with control box 30 which generates a signal which is addressed to motor 31 of motor control valve 32. When there is an imbalance in downstream pressures in lines 10 and 14 the diaphragm 28 will be moved upwardly or downwardly and its follower 29 will move to a different point on the slide wire of controller 30.

Figure 5:
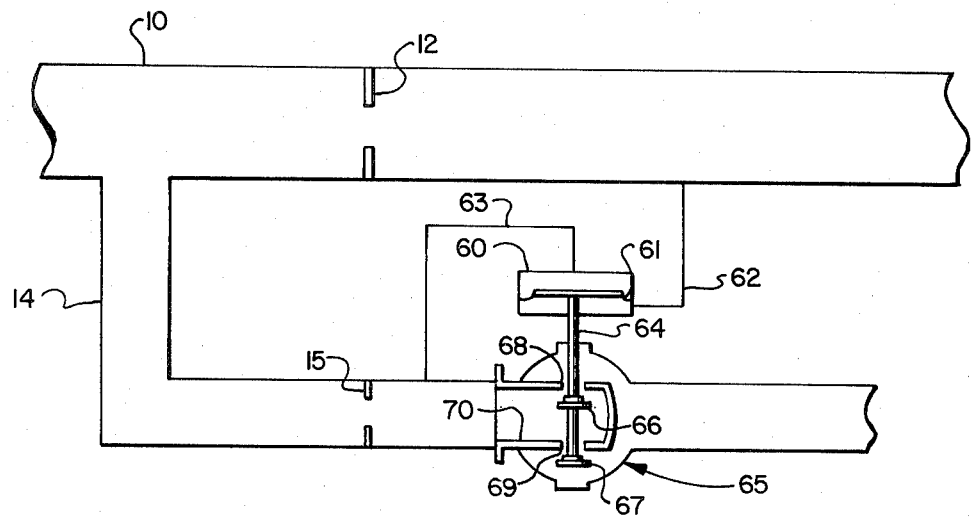
FIG. 5 is a diagramatic elevational view of yet another alternate form of the equipment for gathering proportionate samples in accordance with the invention.

Attention is now directed to FIG. 5 which illustrates still another means for establishing the pressure downstream of orifices 12 and 15 at the same level. A diaphragm housing 60 is provided, surrounding flexible diaphragm 61. The lower side of housing 60 is connected by line 62 to main pipeline 10 at a point downstream from orifice 12. The upper side of housing 60 is connected by line 63 to sample line 14 at a point downstream of orifice 15. Thus diaphragm 61 is in pressure communication with the two pressures of interest, those just downstream of the two orifice plates. The position of diaphragm 61 within housing 60 is thus a function of the two downstream pressures.

A control rod 64 is connected to diaphragm 61 and passes through an opening in housing 60 and into valve 65 provided in sample line 14. Rod 64 carries valve plates 65, 66, which are seatable in valve openings 67, 68 respectively in valve body 70.

In operation, if the downstream pressure in mainline 10 is greater than that in sample line 14, diaphragm 61 tends to close valve 65 and increase the pressure in line 14. If the downstream pressure in line 14 is greater, diaphragm 61 tends to open valve 65 to reduce that pressure. Thus the two pressures of interest tend to be equalized.

Returning now to FIG. 1 it can be seen that downstream of motorized valve 22 in sample line 14 there is provided a ballast tank 33. The purpose of the ballast tank is to smooth irregularities in flow resulting from excursions of piston 19 in line 18. The size of ballast tank 33 need only be relatively large compared to the volume of line 18 lying between microswitch contacts 20 and 21. If equipment such as that shown in FIGS. 3 and 4 employed in the sample taking and establishing equipment, the surges in flow are likely to be smaller than that involved in the equipment of FIG. 1, and it may thus be possible to dispense with ballast tank 33 or to use a smaller tank.

The flowing gas sample is led from ballast or surge tank 33 through line 34 to branch lines 35 and 36 where it is divided into two streams for delivery to two burners 39–40. A capillary 37 is in line 35 and a similar capillary 38 is in line 36.

Air is also delivered to burners 39–40 through an especially designed flow-control system of the kind disclosed in above mentioned U.S. Pat. No. 4,285,245. Air enters the system through line 41 and passes through flow control and measurement system 42. A major component of that system is motorized valve 56. The air then passes into chamber 43 where its pressure is sensed by transducer 44. Flowing air leaving the chamber passes through pressure regulator 46 and capillary into line 48. Flow line 48 is divided into lines 49 and 50 which lead respectively to burners 39 and 40. A capillary 51 is provided in line 49 and a capillary 52 is provided in line 50.

The rate of flow of energy into the flames of burners 39, 40 when their average temperature is at a maximum is in direct proportion to the rate of air flow to those burners. This is an alternate way of stating the principal underlying the equipment just described as well as the equipment for determining the caloriforic value of a fuel gas described and shown in the above listed patents. In effect, in the equipment shown in FIG. 1 the fuel flow to the burners is "titrated" with air, using the maximum flame temperature as detected by thrermocouples 53 and 54 to determine the end point. The measured rate of air flow is then in proportion to the rate of energy flow of the gas flowing in sample conduit 14, and because of the proportionality of that gas flow rate to the gas flow rate in the main pipeline, the air flow rate as measured is also in constant proportion to the energy flow rate in main pipeline 10.

The detected thermocouple signals from thermocouples 53, 54 are delivered to microcomputer 55 which processes them and sends appropriate derivative signals to control system 45 of the flow meter. In response to the signals it receives, the control system varies the setting of regulator valve 46 to increase or decrease the air flow to traverse it across the range of flow which produces a detectable maximum average temperature at the thermocouples. Upstream motorized valve 56 is closed periodically by the control system and the pressure fall in chamber 43 is detected by pressure transducer 44 to provide a reading of the air flow rate, since the slope of the time decay of pressure in tube 43 is proportional to flow rate, as is explained in greater detail in U.S. Pat. No. 4,285,245.

In accordance with the invention other forms of flow measuring equipment may be employed for measuring the air flow rate. These alternate forms of air flow measurement include hot wire flow meters, orifice plate flow meters, rotometers, displacement meters of various sorts, and the like.

Instead of monitoring the flame temperature to establish a flow rate producing a maximum flame temperature, the oxygen flow, or lack thereof in the exhaust immediately downstream from a burner may be monitored instead. Zirchonium dioxide oxygen detectors are suitable for this purpose. When oxygen content in the exhaust gas is the detected parameter, only a single burner is employed, and the gas and air flow to the other burner in a unit may be terminated by suitable valves. In one embodiment employing exhaust gas oxygen monitoring, the desired end point is a sharp decrease in oxygen content in the exhaust gas, which means the air flow rate is producing a stoichiometric mixture. In another form of the invention in which oxygen flow in the exhaust gas is measured, the air flow rate is deliberately established at a rate confidently expected to be in excess of the stoichiometric amount, and the residual or remnant or excess oxygen flow in the exhaust gas is monitored to yield a parameter which is a known or calculatable function of the total energy flow rate in the main pipe line.

Returning now to FIG. 1, the equipment thereon for practicing the invention in accordance with the two alternate modes just discussed may be pointed out. In the exhuast gas lines above the burners are mounted zirconium dioxide oxygen detectors 80, 81, which are devices whose electrical output essentially switches from "on" to "off" when the stoichiometric point of oxygen content is crossed from rich to lean, thus providing a clear signal for that point. Also mounted in the exhaust lines are flow meters 82, 83, indicated very diagrammatically as orifice plates in FIG. 1, although various sorts of flow meters may be used. The flow meters, in conjunction with the oxygen detectors, provide the data necessary for determining oxygen flow in the excess oxygen mode of operation.

Figure 6:
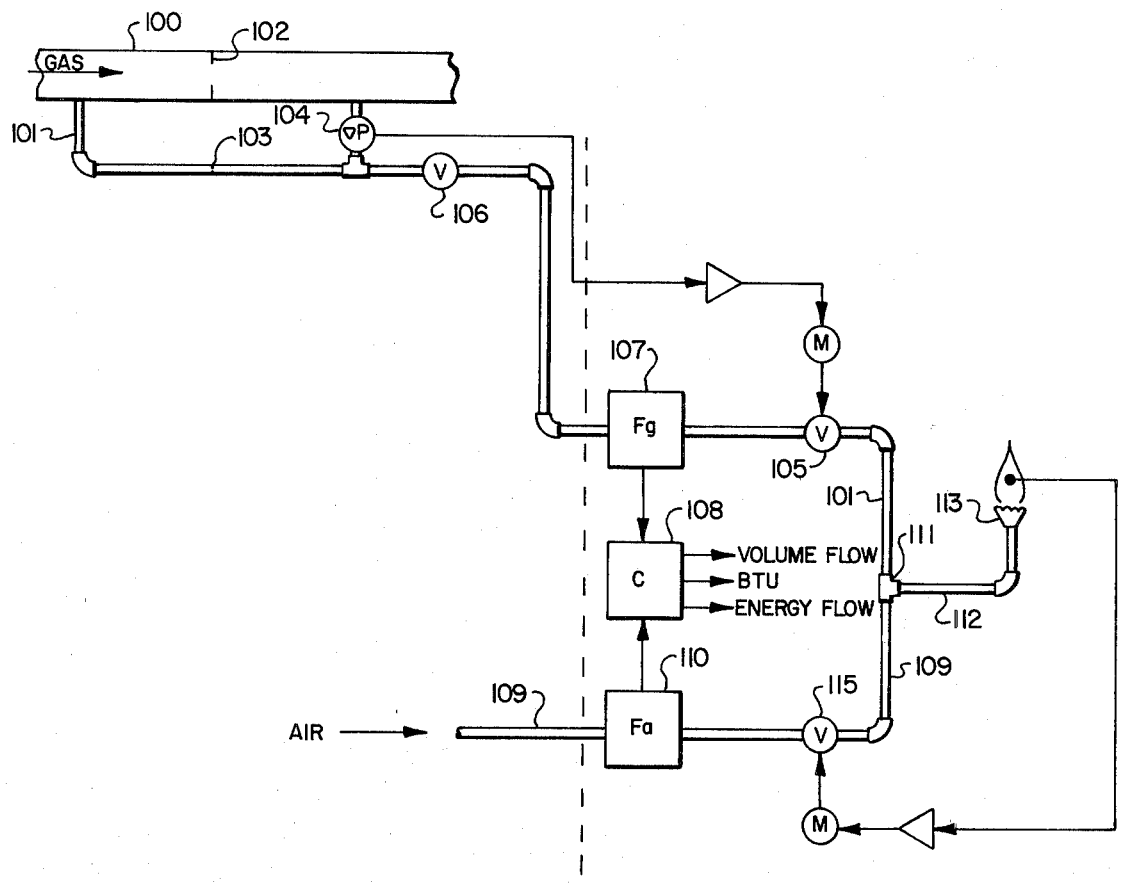
FIG. 6 is a diagramatic elevational view of another embodiment of the invention.

Attention is now directed to FIG. 6 which illustrates another embodiment of the invention. In FIG. 6, the main pipeline is designated 100, while the sample line is designated 101. Orifice plate 102 is mounted in the main line, and orifice plate 103 in the sample line. The pressure downstream of these plates are detected by differential pressure sensor 104. The output signal from sensor 104 is amplified and employed to control motorized valve 105 to adjust the gas flow to equalize the downstream main line and sample line pressures. Sample line 101 also contains a regulator valve 106, and a flowmeter 107 of suitable type, indicated diagrammatically as a box Fg. The output signals from the flowmeter are delivered to a control computer 108, indicated diagrammatically as a box C.

An air line 109 is provided with a flow meter 110, indicated diagrammatically as box Fa, installed therein. Signals from flowmeter 110 are delivered to computer 108. Air line 109 and gas sample line 101 join at 111 to deliver a combustible mixture through line 112 to burner 113. A detector 114 is positioned in or adjacent the flame to detect maximum temperature (if a thermocouple) or stoichiometric point (if a zirconium dioxide detector). The signal from detector 114 is amplified and employed to control motorized valve 115 to adjust the air flow to the desired end point.

In operation, the gas flow rate reported by gas meter Fg is proportional to volume flow in pipeline 100. The air flow rate reported by air meter Fa is proportional to energy flow rate in pipeline 100. The ratio of the air flow rate to the gas flow rate (Fa/Fg) is proportional to heat content per standard unit of volume. Computer 108 may be programmed to compute this ratio, as well as to apply proportionality constants to place the data Fg, Fa, and Fa/Fg in the desired units.

In addition to providing a continuous measurement of energy flow in the pipeline, parts of the system can be used to measure volumetric flow in the pipeline. This can be done much more accurately with this invention than with state of the art methods. The output from conduit 14 (see FIG. 1) can be measured at ambient pressure with a volumetric displacement meter. With the correct proportionality constant this output can then give the integrated volume flow through the main pipeline measured at standard conditions. A time derivative of this volume will give the flow rate. Such a determination of flow rate would be independent of gas properties and would require the measurement of only one parameter instead of several.

We claim:

1. A method for determining the rate of energy flow in a combustible gas flowing in a line comprising:
   (a) taking a flowing sample of said combustible gas at a rate constantly proportionate to the flow rate of said gas flowing in said line;
   (b) combusting said flowing gas sample with a flowing stream of combustion supporting gas;
   (c) varying the flow rate of said combustion supporting gas while measuring a parameter of said combustion supporting gas flow rate to identify a magnitude for said parameter indicative of a flow rate for said combustion supporting gas which is proportional to the rate of energy flow in said combustible gas flowing in said line; and
   (d) measuring the flow rate of said combustion supporting gas producing said parameter magnitude.

2. A method in accordance with claim 1 in which said parameter is combustion temperature.

3. A method in accordance with claim 1 in which said parameter is exhaust gas oxygen concentration.

4. A method for determining the rate of energy flow in a combustible gas flowing in a line comprising:
   (a) taking a flowing sample of said combustible gas at a rate constantly proportionate to the flow rate of said gas flowing in said line;
   (b) combusting said flowing gas sample with a flowing stream of air;
   (c) adjusting the flow rate of said flowing stream of air until the combustion temperature is a maximum; and
   (d) measuring the adjusted flow rate of said air stream, which is proportional to the rate of energy flow in said combustible gas flowing in said line;

5. A method for determining the rate of energy flow in a combustible gas flowing in a line comprising:
   (a) taking a flowing sample of said combustible gas at a rate constantly proportionate to the flow rate of said gas flowing in said line;
   (b) combusting said flowing gas sample with a flowing stream of air;
   (c) adjusting the flow rate of said flowing stream of air until air is being flowed for supporting combustion at a stoichiometric rate; and
   (d) measuring the adjusted flow rate of said air stream, which is proportional to the rate of energy flow in said combustible gas flowing in said line.

6. A method for determining the rate of energy flow in a combustible gas flowing in a line comprising:
   (a) taking a flowing sample of said combustible gas, at a rate constantly proportionate to the rate of said gas flowing in said line;
   (b) combusting said flowing gas sample with a flowing stream of combustion supporting gas flowing at a selected rate in excess of stoichiometric; and
   (d) measuring the flow rate of oxygen in the combustion product stream.

7. Apparatus for determining the rate of energy flow in a combustible gas flowing in a line comprising:
   (a) means for taking a flowing sample of said combustible gas at a rate constantly proportionate to the flow rate of said gas flowing in said line;
   (b) means for combusting said flowing gas sample with a flowing stream of air;
   (c) means for adjusting the flow rate of said flowing stream of air until the combustion temperature is a maximum; and
   (d) means for measuring adjusted flow rate of said air stream, which is proportional to the rate of energy flow in said combustible gas flowing in said line.

8. An apparatus in accordance with claim 7 in which said means for taking said flowing sample comprise:
   (a) a first flow restriction in said line;
   (b) a sample line connected to said line upstream of said first flow restriction;
   (c) a second flow restriction in said sample line; and
   (d) means for equalizing the pressures downstream of said first and second flow restrictions.

9. An apparatus in accordance with claim 7 in which said means for adjusting the flow rate of said flowing stream of air comprise:
   (a) thermocouple means for determining said combustion temperature;
   (b) a motorized valve in position to intercept said flowing stream of air; and
   (c) means responsive to said thermocouple means for operating said valve in a direction to maximize the temperature signal from said thermocouple.

10. Apparatus for determining the rate of energy flow in a combustible gas flowing in a line comprising:
    (a) means for taking a flowing sample of said combustible gas at a rate constantly proportionate to the flow rate of said gas flowing in said line;
    (b) means for combusting said flowing gas sample with a flowing stream of air;
    (c) means for adjusting the flow rate of said flowing stream of air until air is being flowed for supporting combustion at a stoichiometric rate; and
    (d) means for measuring the adjusted flow rate of said air stream, which is proportional to the rat of energy flow in said combustible gas flowing in said line.

11. An apparatus in accordance with claim 10 in which said means for taking said flowing sample comprise:
   (a) a first flow restriction in said line;
   (b) a sample line connected to said line upstream of said first flow restriction
   (c) a second flow restriction in said sample line; and
   (d) means for equalizing the pressures downstream of said first and second flow restrictions.

12. An apparatus in accordance with claim 10 in which said means for adjusting the flow rate of said flowing stream of air comprise:
   (a) a zirconium dioxide detector means for determining said stoichiometric rate;
   (b) a motorized valve in position to intercept said flowing stream of air; and
   (c) means responsive to said detector means for operating said valve in a direction to maximize the rate of fall of the oxygen signal from said detector.

* * * * *